United States Patent
Ciani

(10) Patent No.: US 8,330,457 B2
(45) Date of Patent: Dec. 11, 2012

(54) DEVICE FOR THE IN-LINE DETECTION OF SURFACE DEFECTS IN A ROLLED PRODUCT IN A ROLLING STAND AND RELATIVE METHOD

(75) Inventor: Lorenzo Ciani, Udine (IT)

(73) Assignee: Danieli Automation SpA, Buttrio (IT)

(*) Notice: Subject to any disclaimer, the term of this patent is extended or adjusted under 35 U.S.C. 154(b) by 707 days.

(21) Appl. No.: 12/520,109

(22) PCT Filed: Dec. 19, 2007

(86) PCT No.: PCT/EP2007/064199
§ 371 (c)(1),
(2), (4) Date: Jun. 19, 2009

(87) PCT Pub. No.: WO2008/074827
PCT Pub. Date: Jun. 26, 2008

(65) Prior Publication Data
US 2009/0309589 A1  Dec. 17, 2009

(30) Foreign Application Priority Data
Dec. 21, 2006 (IT) .................. UD06A0271

(51) Int. Cl.
G01N 27/82 (2006.01)
(52) U.S. Cl. ...................... 324/238; 324/240

(58) Field of Classification Search .............. 324/238, 324/240–242
See application file for complete search history.

(56) References Cited

FOREIGN PATENT DOCUMENTS

| EP | 0995507 A2 | 4/2000 |
|----|------------|--------|
| FR | 2131872 A1 | 11/1972 |
| FR | 2426257 A2 | 12/1979 |
| FR | 2674459 A1 | 10/1992 |
| FR | 2686699 A1 | 7/1993 |
| JP | 61118654 A | 6/1986 |

*Primary Examiner* — Bot Ledynh
(74) *Attorney, Agent, or Firm* — Panitch Schwarze Belisario & Nadel LLP

(57) ABSTRACT

A device (10) for the in-line detection of surface defects of a rolled product (30) in a rolling stand (11, 111) comprises an inspection unit (19) having one or more coils (20, 21) able to generate and detect magnetic fields. The rolling-stand (11, 111) is provided with a support structure (28) supporting rolling means (12, 112) that are provided for effecting a roll-mill process on said product (30), a guide element (13) having a guide hole (14) defining a nominal rolling axis (X) and a support unit (15, 115), assembled on the support structure (28) and which is provided as a structural element of the rolling stand (11, 111) that supports said guide element (13). The inspection unit (19) is assembled on said support unit (15, 115), in order to be directly housed and integrated in the structural element already present in the rolling stand (11, 111).

12 Claims, 3 Drawing Sheets

DEVICE FOR THE IN-LINE DETECTION OF SURFACE DEFECTS IN A ROLLED PRODUCT IN A ROLLING STAND AND RELATIVE METHOD

CROSS-REFERENCE TO RELATED APPLICATION

This application is a section 371 of International Application No. PCT/EP2007/064199, filed Dec. 19, 2007, which was published in the English language on Jun. 26, 2008 under International Publication No. WO 2008/074827 A1 and the disclosure of which is incorporated herein by reference.

FIELD OF THE INVENTION

The present invention concerns a device for the in-line detection of surface defects in a rolled product in a continuous rolling stand, and the relative detection method.

In the following description, by rolled product we also mean a product made by means of similar or comparable processes, such as drawing or extrusion.

Moreover, even though the invention is applied preferentially to products with a circular nominal section, it is also applied with rolled products of different section, such as polygonal, curvilinear, lobed or other.

BACKGROUND OF THE INVENTION

A method is known, in the state of the art, for the in-line detection of surface defects present on bars or wire during rolling, drawing or extrusion operations, or at the end of them. This known method provides to use electromagnetic device's that are disposed downstream of the rolling line, or downstream of a relative rolling unit and which, by means of coils able to generate an electromagnetic field and relative reception coils, detect the presence of surface defects, such as cracks, inclusions, microfissures.

Detection devices of the electromagnetic type as above cited are disclosed in the French applications FR-A-2.131.872, FR-2.686.699 and FR-A-2.426.257, in the European patent application EP-A-0.995.507 and in the Japanese patent application JP-A-61.118.654.

In general, in methods based on the use of coils, in order to obtain highly sensitive detection of the defects, the so-called filling factor plays an important role. The filling factor is the ratio between the area of the central hole of the coils through which the rolled product passes, and the area of the cross section of the rolled product. The higher the filling factor, the more sensitive the device. On the other hand, when the filling factor is high, the risks of contact of the rolled product increase, in particular if it is subject to vibrations and transverse movements with respect to its axis, against the internal wall of the hole of the coils, with consequent possible damage and loss of sensitivity of detection.

One disadvantage of this known method is that, since detection of this type is sensitive to the transverse movements of the rolled product, it is not possible to guarantee precise results due to the vibrations to which the rolled product is subject when it is no longer guided inside the relative rolling unit and due to the fact that, for this reason too, the filling factor cannot have a high value, near to the unit, due to the risks of contact mentioned above.

This low sensitivity leads to medium to small surface detects being overlooked, for example those less than 2% of the diameter of the rolled product, because they are not accurately detected.

Another disadvantage of known detection devices is that they require purpose-made installation structures, which must be re-equipped and prepared every time the rolling units are reconfigured for a new format of the rolled product being worked.

Another known detection device, suffering of the above mentioned disadvantages, is disclosed in the French application FR-A-2.674.459, wherein an inspection group, provided with detection electromagnetic coils of the type as above discussed, is interposed between two guide elements, an upstream guide element and a downstream guide element. This is a traditional arrangement that requires a dedicated installation and that is completely independent and separated from the rolling, drawings or extrusion devices that are usually upstream or downstream disposed.

Purpose of the present invention is to achieve a device, and perfect a relative method, for the in-line detection of surface defects in a rolled product which allows a highly sensitive detection of the defects, in continuous rolling lines, and which reduces the times needed for configuration and re-equipping compared with known systems.

The Applicant has devised, tested and embodied the present invention to overcome the shortcomings of the state of the art and to obtain these and other purposes and advantages.

SUMMARY OF THE INVENTION

The present invention is set forth and characterized in the independent claims, while the dependent claims describe other characteristics of the invention or variants to the main inventive idea.

In accordance with the above purposes, a device for the in-line detection of surface defects in a rolled product is usable in a rolling unit or stand having a support structure to support rolling means that are provided for effecting a roll-mill process on said product, such as rolls, cylinders or rings, at least a guide element having a guide hole defining a nominal rolling axis and a support unit, assembled on said support structure and which is provided as a conventional structural element of the rolling stand and supports the guide element.

The device for detecting defects is of the type comprising an inspection unit having one or more detection coils able to generate and detect magnetic fields, in a manner known to the state of the art.

According to a characteristic feature of the present invention, the inspection unit is assembled on the support unit, that is, in other words, it is directly housed and integrated in the structural element already present in the rolling stand.

Thanks to this assembly position of the inspection unit and the relative coils, the step to detect defects is carried out almost concomitantly with the rolling step on the same segment of the moving bar, on a rolled product which is therefore perfectly guided, stable, scarcely susceptible to transverse vibrations or oscillations with respect to the nominal rolling axis and not subject to external influences which can alter the detection of the defects and make it less reliable.

Advantageously, therefore, the defects detected include the so-called "small" defects, that is, with a nominal size less than 2% of the diameter of the rolled product.

The present invention advantageously exploits the correct guidance, along the nominal rolling axis, of the rolled product at outlet from, and possibly at inlet to, the rolling operation. The so obtained correct and perfect alignment of the axis of the rolled product with the axis along which inspection is carried out also allows to keep a high and constant filling factor and at the same time to reduce, and even eliminate, the risks of contact with the internal wall of the hole of the coils.

Moreover, the device according to the present invention ensures high stability and balance of the rolled product and a high ratio between signal and noise, all of which determines a highly sensitive detection of the defects.

The assembly and installation of the coils to detect the defects directly on a support element conventionally already present in the rolling stand also allows to exploit the cooling systems already present in said apparatus, and other possible accessory plants that are associated with the rolling stand, in order to maintain the detection coils in correct functioning conditions.

Another advantage of the present invention is that re-equipping the rolling stand, for example to change format, size or other, also determines the simultaneous assembly and installation of the device to detect defects. Therefore, the re-equipping does not require onerous additional operations, and also prevents the occurrence of assembly errors which can happen, with known devices, when it is necessary to install a device to detect defects that is separate and autonomous with respect to the rolling stand.

Moreover, the invention requires simple maintenance and can be integrated with other automation systems present.

According to an embodiment, the devices comprises an assembly which is assembled on said support unit and which defines a seating aligned with said axis, in which said inspection unit is able to be housed, the seating having an opening in direct connection with the guide hole, said inspection unit being provided with a hole, aligned along said axis, around which said coils are disposed, and through which said rolled product is able to pass, wherein the hole opens, through the opening of the seat, toward the guide hole and is coaxial therewith.

BRIEF DESCRIPTION OF THE DRAWINGS

These and other characteristics of the present invention will become apparent from the following description of a preferential form of embodiment, given as a non-restrictive example with reference to the attached drawings wherein.

DETAILED DESCRIPTION OF A PREFERENTIAL FORM OF EMBODIMENT

Figure 3:
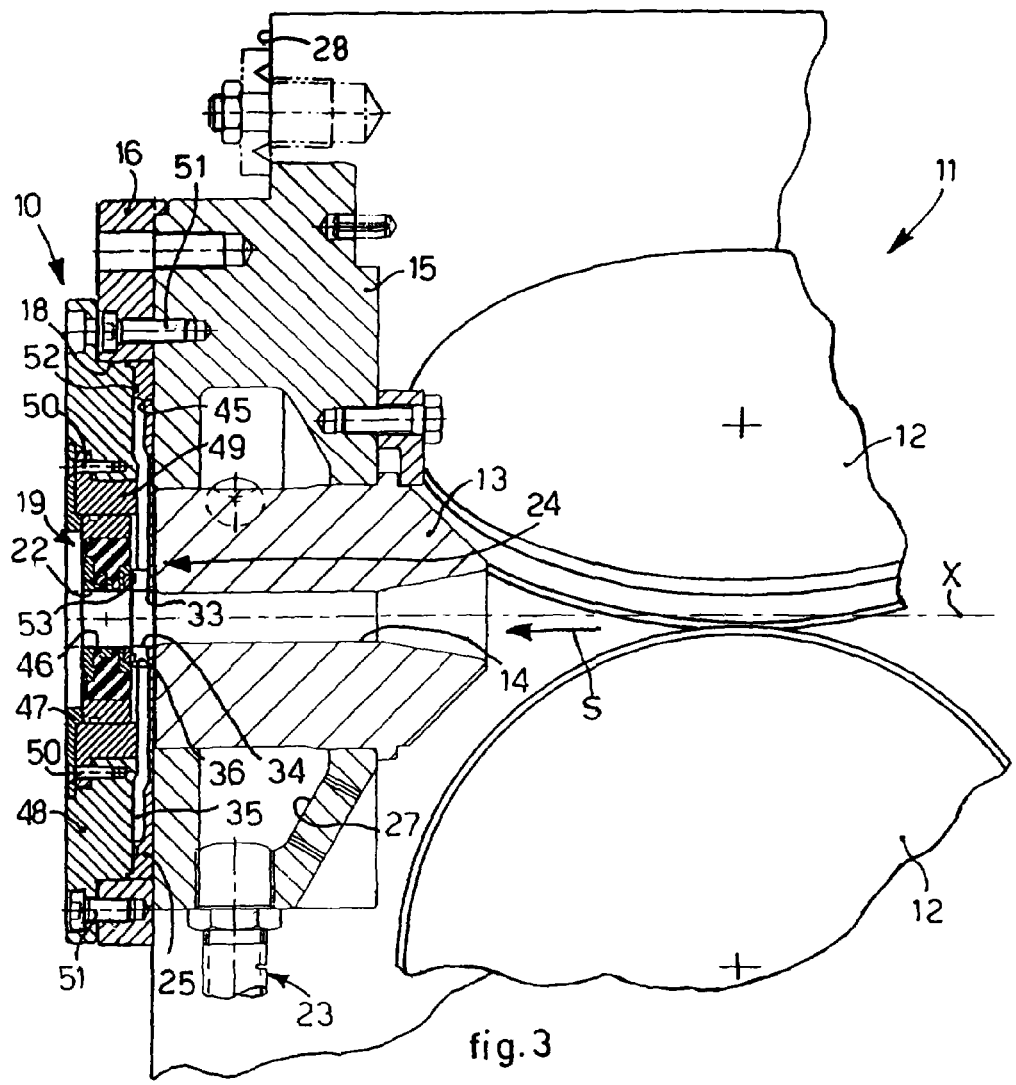
FIG. 3 is a section from III to III of FIG. 1.
Figure 5:
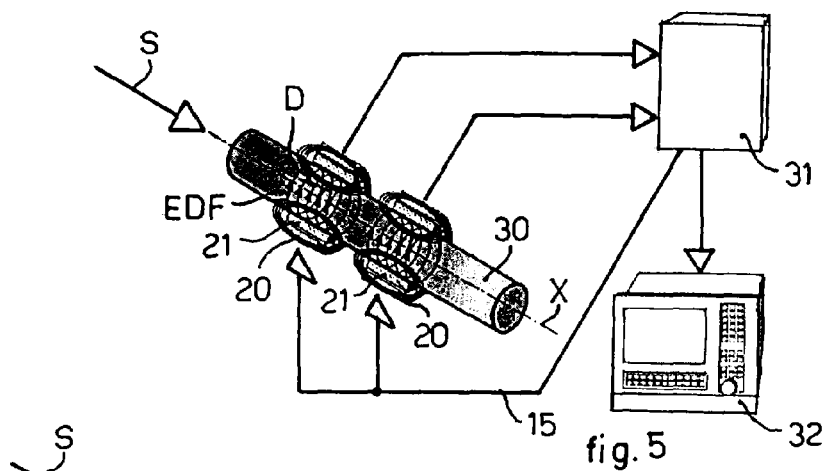
FIG. 5 is a schematic representation of the functioning of the device according to the present invention.

With reference to FIG. 3, a device 10 for the in-line detection of surface defects D of a bar 30 (FIG. 5) is used in a rolling stand, or rolling module, 11 (FIG. 3) of the Kocks® type, having three rolling rings 12 disposed at 120° with respect to each other, in order to produce rolled bars 30. Each rolling stand 11 is used as a module, to form a train typically comprising five modules in series; the stands 11 are disposed aligned with each other along a nominal rolling axis X. Each stand 11 comprises a suitable support structure 28 on which the rolling rings 12 and the other equipment described hereafter are assembled. Downstream of the rolling rings 12 a guide 13 is disposed, also assembled on the support structure 28, which receives the bar 30 emerging in the direction of the arrow S (FIG. 3) from each exit of each previous rolling stand 11, and accompanies it towards the subsequent rolling stand 11.

The guide 13 is tubular in shape and a relative guide hole or pipe 14 substantially defines the nominal rolling axis X. The guide 13 is supported by a support plate 15, attached directly on the structure 28 of the rolling stand 11. The support plate 15 has a surface 45 facing towards the outside of the rolling stand 11, through which the guide hole 14 leads.

Figure 1:
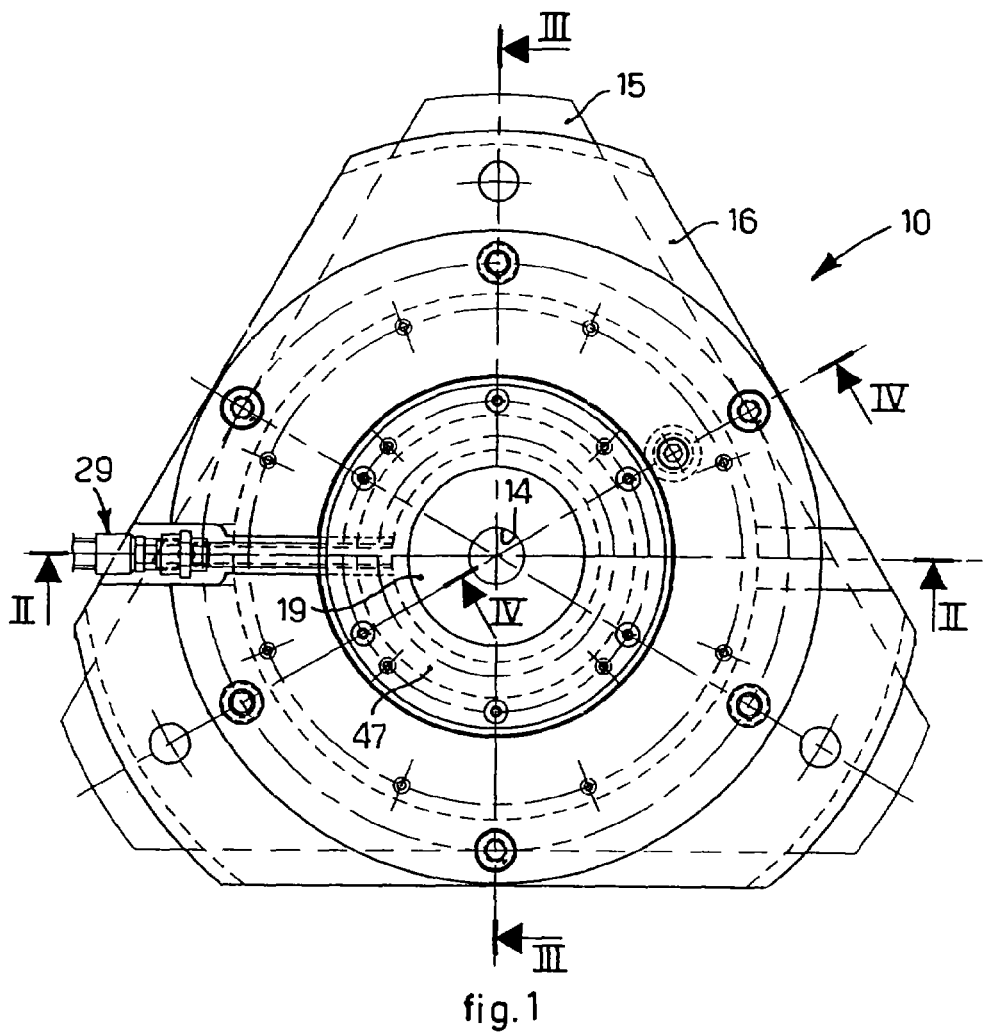
FIG. 1 is a partial front view on the exit side of the rolled product of a rolling stand of the type with three rings provided with a device to detect surface defects according to the present invention.
Figure 2:
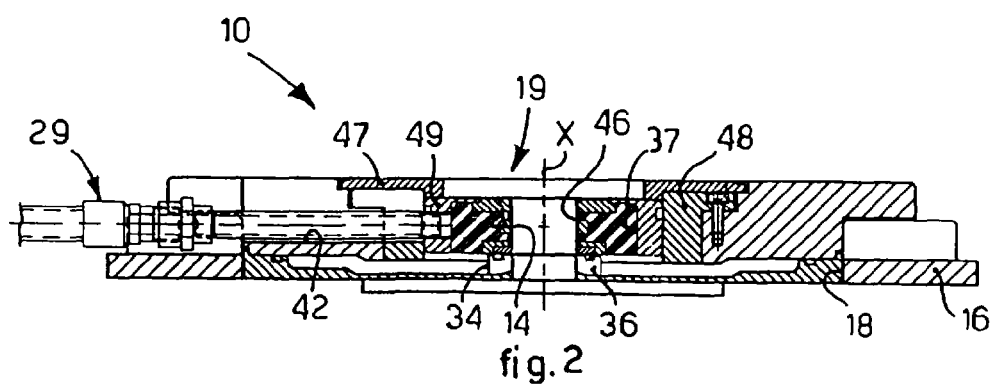
FIG. 2 is a section from II to II of FIG. 1.

A seating or compartment 18 is made by applying, directly on the surface 45, a centrally holed plate 16 (FIGS. 1, 2 and 3) and connected to the support plate 15 by means of attachment screws 51. The compartment 18 is thus made in correspondence with the outlet of the guide hole 14.

Figure 4:
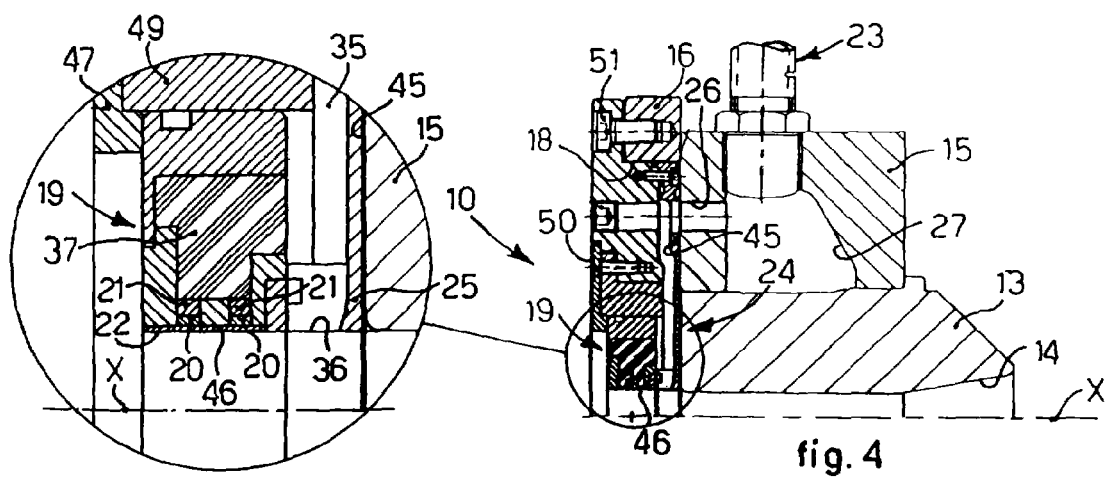
FIG. 4 is a section from IV to IV of FIG. 1 with relative enlarged detail.

The defect detection device 10 comprises an inspection unit 19, comprising magnetic coils 20, 21 (FIG. 4), the functioning of which is described in greater detail hereafter. The inspection unit 19 is discoid in shape and is made of electrically insulating material.

The inspection unit 19 is housed in the compartment 18 made in said plate 16, and is held in place and centered with respect to the guide hole 14 using a flange 48 (FIGS. 2 and 3), of suitable size, which reduces the actual sizes of the compartment 18.

In order to adapt to the various sizes of the inspection unit 19, as required according to the rolling application, for example the format of the bar 30, the invention also provides one or more adapter/reducer rings 49 (FIGS. 2, 3 and 4) which are inserted into the flange 48 and which, when used, further reduce the effective sizes of the compartment 18 in which the inspection unit 19 is located. The flange 48 and the possible adapter/reducer ring 49 are shaped so as to determine a groove 42, which houses the electric cable 29 that carries the electric signals detected by the inspection unit 19.

The inspection unit 19 is clamped inside the compartment 18 by means of a suitable cover 47, axially holed. The cover 47, by means of attachment screws 50, cooperates both with the possible adapter/reducer ring 49, and also with the flange 48.

According to the invention, the inspection unit 19 is provided with a central hole, or inspection channel 22, which is coaxial with the guide hole 14 and through which the bar 30 passes. The inspection channel 22 is protected from the high temperature of the bar 30 by means of a tubular element 46 made of suitable metal material. Moreover, the inspection channel 22 is made in sizes suitable to guarantee the safe transit of the bar 30 and to reduce the risk of contact and jamming of the bar 30, in particular preventing risks of friction. In particular, the diameter of the inspection channel 22 is slightly larger, for example by about 1 millimeter, than the diameter of the guide hole 14 which is sized to be just slightly larger than the nominal diameter of the bar 30 being worked, emerging from the relative rolling pass. Thanks to this sizing, on the one hand a high and optimum filling factor is guaranteed, and on the other hand the risks of contact between the bar 30 and the walls of the inspection channel 22 are substantially eliminated.

Inside the inspection unit 19, and wound around the channel 22, are housed the two reception or pick up coils 20, and two transmission coils 21 (FIG. 5), drowned in a resinous material 37 (FIGS. 2 and 4) which protects them and guarantees their mechanical stability.

The two transmission coils 21 are adjacent and a current flows through them, suitably generated by means of a signal processor 31 (FIG. 5), to induce in the bar 30 to be inspected two variable flows of magnetic field. The magnetic flows induced generate on the surface of the material two distinct adjacent parasite currents, or eddy currents, indicated by EDF in FIG. 5. The parasite currents in turn generate two magnetic fields that induce on the reception coils 20 two corresponding electric currents. The detection of the electric currents on the coils 20 and 21 allows to detect, in a known manner, the surface defects on the bar 30.

The currents circulating on the reception coils 20 are transmitted, by means of the electric cable 29 (FIGS. 1 and 2), to the signal processor 31 which transforms them into information on the presence and type of defects and makes the information available by means of a terminal 32 (FIG. 5) to an operator in charge of controlling the line.

The rolling stand 11 is provided with a plant to deliver cooling water, suitably pre-filtered, having a pipe 23 (FIG. 3) able to be connected to a delivery pipe of a water distribution network. The pipe 23 delivers the water into a suitable distribution chamber 27 of the toroidal type, which surrounds the guide 13, to cool it.

To exploit the cooling water distribution plant already provided on the rolling stand 11, the device 10 advantageously comprises a water distribution circuit 24 (FIGS. 3 and 4), hydraulically connected to the inspection chamber 27 and able to direct the cooling water also to the center of the inspection channel 22 in order to cool it.

In this case, the distribution circuit 24 comprises a pipe 26 (FIG. 4), made in the support plate 15 in order to connect the distribution chamber 27 hydraulically with the compartment 18 where the inspection unit 19 is housed.

Moreover, the distribution circuit 24 is provided with a spray cover 25, of the plate type, which is disposed in the compartment 18 between the inspection unit 19 and the surface 45 of the support plate 15 and which thus determines an interspace 35 in the compartment 18.

The spray cover 25 is provided with a central hole 33 for the passage of the bar 30, and with an annular edge or ridge 34 (FIGS. 2 and 3) which extends from the cover 25, coaxial with the central hole 33, and which, when it is assembled with the inspection unit 19, also functions as a support element for the latter.

The annular edge 34 is provided with distribution channels or notches 36, for example 4 or more channels, disposed involute or helical, in order to increase the turbulence of the water and hence the efficiency of the heat exchange. The channels 36 receive the cooling water from the interspace 35 and direct it towards the inspection channel 22, in order to cool it, and thus cool the inspection unit 19 in its entirety.

The cooling water thus passes from the distribution chamber 27 through the pipe 26 and from here, through the interspace 35, enters into the distribution channels 36 and passes into the channel 22.

A packing element 53, of the O-ring type, is disposed between the cover 25 and the inspection unit 19, while another packing element 52, of the O-ring type, is disposed between the cover 25 and the flange 48.

The device 10 is normally assembled on the last rolling module of the rolling train. In an advantageous variant, it can be assembled on the penultimate module, in order to allow, if the change of format provides only the replacement or also the elimination of the last) module only, to re-equip the machine without intervening on the device 10. If the device 10 is assembled on the last module, instead of the cover 47, the typical outlet funnel of the stands 11 is applied, not shown in the drawings.

Figure 6:
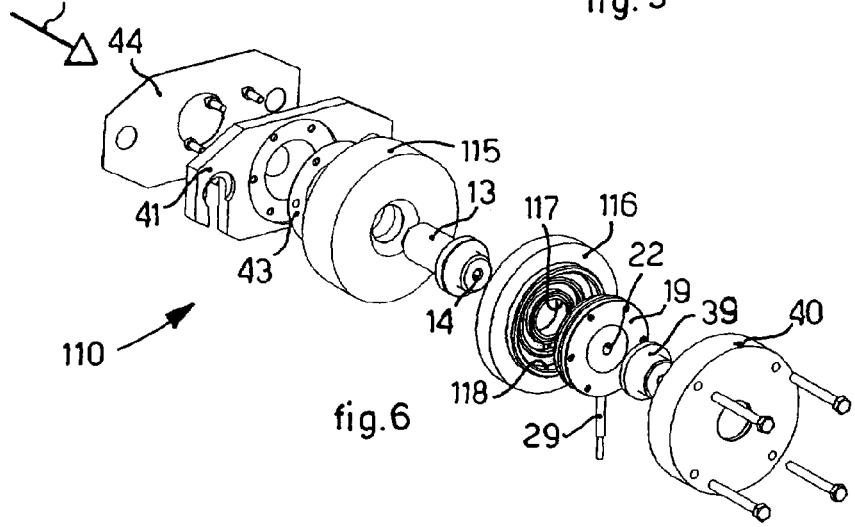
FIG. 6 is a view with separate parts of a variant of the device according to the present invention.
Figure 7:
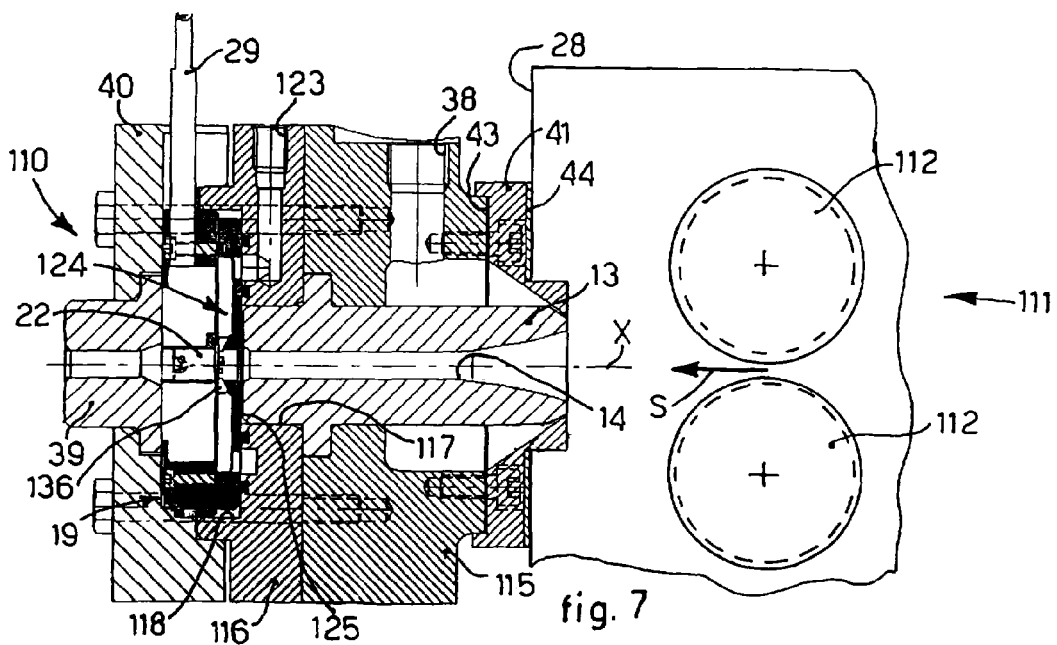
FIG. 7 is a section of a rolling stand of the BGV® type to which the device in FIG. 6 is applicable.

According to another advantageous application, the device according to the present invention, indicated for convenience by the reference number 110 in FIGS. 6 and 7, can be used in rolling stands 111 with two rings 112, of the BGV® type.

In the stand 111, the relative support structure 28 supports the rings 112 and, by means of an attachment head 41, supports a support unit 115 for the guide 13. Between the attachment head 41 and the support unit 115 a spacer 43 is disposed, while a packing element 44 is provided between the attachment head 41 and the support structure 28.

The inspection unit 19 is assembled directly at outlet from the guide 13, by means of a support plate 116, with the same function as the plate 16, seen previously for the Kocks® application. The plate 116 is assembled on the support unit 115 and is provided with an axial hole 117, into which the guide 13 is partly inserted. Moreover, on the plate 116, in particular on its front side, a seating or compartment 118 is made, to house the inspection unit 19 and the relative electric cable 29.

In the application to the stand 111 of the BGV® type, a guide 39 is also provided at outlet from the inspection unit 19. The inspection channel 22, in this case too, has a diameter slightly greater than the diameter of the inlet guide 13 and outlet guide 39. The whole is kept assembled by means of a closing cover 40.

The support unit 115 also functions as a dryer, by means of which, thanks to a pipe 38 which delivers a flow of air, the cooling water drawn by the bar and/or arriving from inside the stand 111 is stopped.

A pipe 123, connected to the cooling water distribution network of the stand 111, not shown in the drawings, is made in the support plate 116 so as to deliver a flow of water, which acts as a coolant for the inspection unit 19.

In the case of the stand 111, we have a distribution circuit 124 defined by a relative spray cover 125, for convenience shown only in FIG. 7, provided with distribution channels 136 which direct the water from the pipe 123 to the inspection unit 19, in order to cool it.

The method for the in-line detection of surface defects comprises the rolling step proper of the bar 30, by means of the rolling rings 12, 112, a guide step of the bar 30 by means of the guide 13, immediately downstream of the rolling rings 12, 112, and a step of detecting the surface defects by means of the coils 20, 21. The detection step is carried out substantially concomitantly on the same segment of the bar 30, that is, in physical proximity and substantially coinciding temporally, with the rolling step and in the guide step which immediately follows and/or precedes the rolling step, so that the bar 30 is perfectly guided.

It is clear that modifications and/or additions of parts and/or steps may be made to the device 10, 110 and the method as described heretofore, without departing from the scope of the present invention.

It is also clear that, although the present invention has been described with reference to some specific examples, a person of skill in the art shall certainly be able to achieve many other equivalent forms of the device and of the relative method, having the characteristics as set forth in the claims and hence all coming within the scope of protection defined thereby.

The invention claimed is:

1. A system of a detection device for in-line detection of surface defects of a rolled product and a rolling stand, said detection device comprising an inspection unit having one or more coils able to generate and detect magnetic fields, said rolling stand being provided with a support structure supporting rolling means for effecting a roll-mill process on said product, a guide element having a guide hole defining a nominal rolling axis (X) and a support unit, assembled on said support structure and which is provided as a structural element of the rolling stand that supports said guide element, wherein said inspection unit is assembled in a seating provided in an assembly element directly assembled on said support unit of said rolling stand, in order to be directly housed and integrated in said structural element already present in the rolling stand.

2. The system as in claim 1, wherein said inspection unit is provided with a first hole, able to be aligned along said axis (X), around which said coils are disposed, and through which said rolled product is able to pass.

3. The system as in claim 2, wherein the first hole of said inspection unit and said guide hole of said guide element are coaxial with each other.

4. The system as in claim 2, wherein the diameter of said first hole is slightly greater than the diameter of said guide hole.

5. The system as in claim 1, further comprising adapter means for adapting the sizes of said seating to the sizes of said inspection unit.

6. The system as in claim 1, wherein said rolling stand comprises delivery means for delivering a cooling liquid into a distribution chamber made in said support unit in order to cool said guide element, the system comprising distribution means hydraulically connected with said delivery means for directing said cooling liquid toward said inspection unit.

7. The system as in claim 6, wherein said distribution means comprises a cover, disposed in said seating so as to achieve a distribution interspace and provided with distribution channels able to receive said cooling liquid from said distribution chamber and to direct the cooling liquid to said inspection unit.

8. The system as in claim 7, wherein said distribution means comprises a pipe which is made through with respect to a surface of said support unit and which hydraulically connects said distribution chamber with said distribution channels.

9. The system as in claim 1, further comprising delivery means for delivering a cooling liquid made in said assembly element in order to direct said cooling liquid toward said inspection unit, through a cover provided with distribution channels.

10. The system as in claim 1, further comprising processing means for processing signals received by said coils and transmitting the signals to electronic display means.

11. A method for the in-line detection of surface defects of a rolled product in a system as in claim 1, comprising a step of rolling said rolled product by said rolling means, a step of guiding said rolled product by said guide element immediately downstream of said rolling means and a step of detecting surface defects by one or more coils, wherein said detection step is carried out substantially concomitantly, on the same segment of said rolled product, with the rolling step and in the guiding step which immediately follows or precedes said rolling step.

12. The system as in claim 1, wherein the support structure surrounds at least a portion of the guide element and at least a portion of the rolling means.

* * * * *